United States Patent [19]

Holy et al.

[11] 4,118,426
[45] Oct. 3, 1978

[54] PRODUCTION OF HYDROXY ETHERS

[75] Inventors: Norman L. Holy, Bowling Green, Ky.; Theodore E. Nalesnik, Yonkers, N.Y.

[73] Assignee: Western Kentucky University, Bowling Green, Ky.

[21] Appl. No.: 795,602

[22] Filed: May 10, 1977

[51] Int. Cl.² .............................................. C07C 41/02
[52] U.S. Cl. ........................... 260/615 B; 260/613 D; 260/613 B; 260/615 R; 560/93; 560/200; 560/209
[58] Field of Search ........... 260/615 R, 615 B, 611 B, 260/613 B, 613 A, 613 D, 612 D

[56] References Cited

U.S. PATENT DOCUMENTS

| 2,327,053 | 8/1943 | Marple et al. | 260/615 R |
| 2,684,387 | 7/1954 | Young | 260/615 R |
| 3,359,331 | 12/1967 | Baker et al. | 260/615 B |
| 3,574,717 | 4/1971 | Lloyd | 260/614 AA |
| 3,714,228 | 1/1973 | Massie | 260/326.14 T |
| 3,931,338 | 1/1976 | Rupilius | 260/615 R |

OTHER PUBLICATIONS

Moiseev et al., Proc. Acad. Sciences USSR, Phys. Chem. Sect., 1960, pp. 115–118.

*Primary Examiner*—Howard T. Mars
*Attorney, Agent, or Firm*—Birch, Stewart, Kolasch and Birch

[57] ABSTRACT

A process for the preparation of hydroxy ethers which comprises reacting an epoxide compound with an organic hydroxy compound in the presence of a $PdCl_2/CuCl_2/O_2$ catalyst system, and recovering the hydroxy ether thus formed from the reaction mixture by a separation step such as distillation. An alternative catalyst system is $K_2PdCl_6/CuCl_2/O_2$.

19 Claims, No Drawings

PRODUCTION OF HYDROXY ETHERS

This invention relates to a process for the production of low molecular weight hydroxy ethers. More particularly, the invention is concerned with a process wherein epoxide compounds are reacted with organic hydroxy compounds in the presence of certain highly active palladium halide containing catalysts, the reaction yielding the valuable low molecular weight hydroxy ethers, particularly useful as solvents.

THE PRIOR ART

U.S. Pat. No. 3,359,331 to Baker et al., issued on Dec. 19, 1967, discusses a reaction between an epoxide and an organic hydroxy compound to yield a hydroxy ether, however, the patentees state that a $PdCl_2$ catalyst fails to bring about any reaction between ethylene oxide and 2-octanol.

U.S. Pat. No. 3,939,213 to Homeier et al., issued on Feb. 16, 1976, is the only other patent in this art known to the inventors which specifically mentions the use of a palladium catalyst, i.e., palladium acetate. However, in the process taught by this patent, the hydroxy ether is formed by a reaction between an epoxide and an olefinic compound rather than the organic hydroxy compound of the present invention.

U.S. Pat. No. 2,327,053 to Marple et al., issued on Aug. 17, 1943, relates to the reaction of an epoxide with an organic hydroxy compound to form a hydroxy ether. The catalysts employed are stannic halides, antimony pentahalides, aluminum halides, zinc halides or ferric halides.

British Pat. No. 322,037 to Gibson et al. discloses a process for manufacturing monoalkyl ethers of ethylene glycol by reacting an aliphatic alcohol with ethylene oxide in the presence of normal sulfates of polyvalent metals, particularly zinc sulfate, nickel sulfate or chromic sulfate.

U.S. Pat. No. 3,931,338 to Rupilius, issued on Jan. 6, 1976, relates to the production of hydroxyalkyl glycol ethers by reacting non-terminal epoxides with ethylene glycol in the presence of an alkoxylation catalyst such as Lewis acids, boron trifluoride adducts, tertiary oxonium salts and compounds with stable carbonium ions. The tertiary oxonium salts can contain halogeno-complex anions such as $BF_4^-$, $FeCl_4^-$, $AlCl_4^-$, $SbCl_6^-$, and $SnCl_6^{2-}$. The compounds with stable carbonium ions can contain the same halogeno-complex anions as the tertiary oxonium salts mentioned above. There is no teaching of employing the $PdCl_6^{2-}$ halogeno-complex anion of the present invention.

OBJECTS OF THE INVENTION

An object of the present invention is to provide a process for producing hydroxy ethers by reacting an epoxide compound with an organic hydroxy compound in the presence of a catalyst which is markedly superior to those known heretofore.

Another object of the invention is to provide a practical and economical process which is adapted to the technical scale production of hydroxy ethers by reaction of epoxide compounds with organic hydroxy compounds.

These and other objects and advantages of the present invention will become apparent to those skilled in the art from a consideration of the following specification and claims.

DETAILED DESCRIPTION OF THE INVENTION

These objectives are accomplished by the process of the present invention which in its broad aspects comprises reacting epoxy compounds such as alkylene oxides and substitution products thereof with organic hydroxy compounds, wherein the hydroxy group may be linked to an aliphatic carbon atom as in alcohols, and effecting the reaction in the presence of the metal halide catalyst. The reaction involved in the production of the hydroxy ethers is shown in the following general equation:

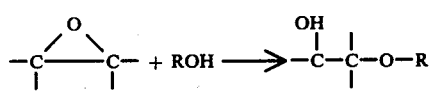

wherein

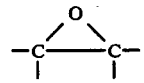

designates the reaction group of the epoxide compound, ROH designates the organic hydroxy compound, and

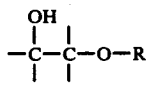

designates essential groups of the product, a hydroxy ether.

THE CATALYST EMPLOYED

It has been found that the reaction can be made to proceed at a practical, rapid rate with a resultant high yield of the desired hydroxy ether if it is conducted in the liquid phase in the presence of palladium chloride ($PdCl_2$) or potassium palladium tetrachloride ($K_2PdCl_4$), and in the additional presence of $CuCl_2$ and molecular oxygen. The oxygen can be pure or diluted, as in atmospheric air. The function of the $CuCl_2$ is to reoxidize the free palladium metal produced by a competing oxidative reaction. An example of this function is shown in the following reaction scheme:

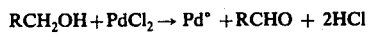

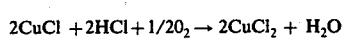

This group of metal halides possesses some peculiar property, not at present understood, which enables them to greatly increase the rate of the liquid phase reaction between the epoxide compounds and the organic hydroxy compounds.

The high catalytic activity of this group of catalysts makes it attractive to employ them in the process of the invention since only small amounts are required in order to obtain a substantial yield of the hydroxy ether product in a relatively short period of time. The actual amount of catalyst needed in the process, however, is dependent upon a number of factors, including the particular metal halide used, the particular reactants employed, the water content of the reaction mixture and the operating conditions utilized. In general, the larger the amount of catalyst present in the reaction mixture, the more rapid will be the reaction. Satisfactory results may be obtained ordinarily with a catalyst concentration in the reaction mixture, with respect to $PdCl_2$, of from a few tenths of one percent to one percent, based upon the weight of the organic hydroxy compound and the epoxide compound in the reaction mixture. If advantageous and desired, more or less than this amount may be used. The molar ratio of $PdCl_2/CuCl_2$ can vary from 0.5 to 2.0. Chloride is not the only anion which can be utilized in the catalyst system. Sulfate or phosphate are suitable replacements for the chloride anion, but some chloride anion must always be present for maintenance of $Pd^{2+}$ in said catalyst system. The oxygen necessary in the catalyst system can be present either as pure oxygen or as atmospheric air. Atmospheric air, if employed, could be present in the range of from 1–10 atmospheres pressure.

The metal halide catalysts employed in the process are all hydrolyzable compounds when in the presence of water. Furthermore, the catalytic activity thereof is considerably impaired when they are in a hydrolyzed condition, and larger amounts of catalyst are required to effect the reaction when the reactants contain appreciable amounts of water as compared to when they are substantially dry. Also, the hydrogen halide liberated by the hydrolysis of the metal halide may combine with the epoxide compound to form halohydrin types of by-products which may prove troublesome to remove the desired product. It is therefore preferable for the reactants used in the process of the invention to be in a substantially anhydrous condition.

THE EPOXIDE COMPOUND REACTANT

The epoxide compounds which may be used in the process of the invention are those which contain not more than four atoms in the heterocyclic epoxide ring, i.e., compounds which contain 1,2- and 1,3-oxide groups such as ethylene oxide, propylene oxide, and trimethylene oxide.

THE HYDROXY-CONTAINING ORGANIC COMPOUND REACTANT

Any hydroxy-containing organic compound containing either an alcoholic hydroxy group or a phenolic hydroxy group may be reacted with the epoxide compound according to the process of this invention, but it is preferable to use one which contains no other groups, other than the hydroxy group, reactive with the epoxide moiety. Either monohydric or polyhydric alcohols or phenols may be used. The alcohols may be either primary, secondary or tertiary in structure, and may be saturated or unsaturated as well as substituted with various substituents. Examples of representative monohydric alcohols include methanol, ethanol, etc.. Among the polyhydric alcohols there may be mentioned ethylene glycol, propylene glycol, etc.. Substituted alcohols include such compounds as ethylene chlorhydrin, propylene bromhydrin, dichlorotertiary-butyl alcohol, etc.. Phenolic compounds include hydroxy compounds such as phenol, ethyl phenol, chlorophenol, etc.. Less preferred hydroxy compounds are those which contain, in addition to the hydroxy group, such groups as carboxyl groups, carboxylic acid groups, etc., which are also reactive with the epoxide compound in competition with the hydroxy group.

OPERATING PARAMETERS

The molecular proportion of the epoxide compound employed in the process of the invention is preferably in considerable excess of the hydroxy compound. If a low molecular weight product is desired, then the hydroxy compound should be employed so as to give a low epoxide/hydroxide compound molar ratio. If it is desired, however, to produce hydroxy ethers of greater molecular weight, then this ratio must be increased. In general, the molar ratio of epoxide/organic hydroxy compound can be in the range of 0.5–10.

The reaction is conducted at temperatures of from about 140° C. to 300° C.. The reaction begins immediately upon contact of the reactants with the catalyst and, while it may initially be slow at the low temperatures, the reaction soon becomes vigorous with a resultant increase in temperature of the reaction mixture. In general, the reaction may be completed by heating the reaction mixture at its normal boiling temperature except when a low boiling reactant such as ethylene oxide, propylene oxide, etc. is employed. In such cases where higher temperatures than the normal boiling point of the reaction mixture are used, it is desirable to maintain a pressure on the reaction mixture at least equal to the total vapor pressure of the mixture at the operating temperature, since the reaction occurs in the liquid phase.

The process of the invention may be executed in a variety of manners and is adaptable to batch-wise, intermittent or continuous operation. For example, a mixture of the epoxide compound and the hydroxide compound is prepared, and may be cooled to a temperature below ordinary room temperature (20°–25° C.). To this mixture the metal halide catalyst is then added, and the mixture may be heated gently. The reaction between the epoxide compound and the hydroxy compound is exothermic, so that the reaction may become sufficiently rapid to evolve a considerable amount of heat which may raise and maintain the temperature at the boiling point for a period of time without further application of external heat. Owing to the spontaneous and possibly violent character of the reaction when using the metal halide catalysts, it may be desirable to apply cooling to the reaction mixture, after initiating the reaction by heating, so as to control it. The reaction may be allowed to proceed satisfactorily with the reaction mixture contained in a vessel fitted with heating and cooling means as well as suitable condensing means, such as a reflux condenser, for condensing and returning any vapors of reactants which may be evolved. In order to assure completion of the reaction, the reaction mixture is heated or boiled for a period of time during which samples may be withdrawn and analyzed to determine when the reaction is substantially complete. The unreacted components of the reaction mixture and the products of the reaction may be separated in any suitable manner such as distillation.

An alternative method of operation is to add the catalyst to the hydroxy compound and subsequently to introduce the epoxide compound either in the entire amount or in portions into the mixture. In general, it is inadvisable to add the catalyst to the epoxide compound in the absence of the hydroxy compound. This procedure is to be avoided because of the tendency of the epoxide compound to react with itself in the presence of the catalyst, thereby forming less valuable and usually undesirable by-products.

Continuous operation may be achieved by passing the mixture of reactants and catalyst through a tubular reactor, for example, at such a rate that substantially complete reaction is obtained during the time of residence of the mixture therein. The reactor is heated by any suitable means so that the mixture is at the desired temperature, and pressure may be applied if necessary to keep the reactants liquid.

EXAMPLES OF THE INVENTION

The following examples are given merely as illustrative of the present invention and are not to be considered as limiting. Unless otherwise indicated, the percentages therein and throughout the application are by weight.

EXAMPLES 1, 2 and 3

A medium-pressure bomb (Parr Instrument Co., Model 425HC) was charged with the desired amounts of alkene oxide, alcohol, catalyst, and a stirring bar. The system was sealed, purged three times with oxygen, then pressurized to 60 psig oxygen pressure and heated to the desired temperature with an oil bath. After the indicated time (Table 1) had elapsed, the reactor was cooled and the contents distilled and identified by IR and NMR.

liquid phase, in a molecular oxygen gaseous atmosphere, and in the presence of a catalytic amount of a catalyst consisting essentially of a palladium salt and a copper salt, at least a portion of the anion of said palladium or copper salt being a chloride ion.

3. A process as recited in claim 2 in which the molar ratio of the epoxide compound to the organic hydroxy compound is in the range of 0.5 to 10.

4. A process as recited in claim 2 in which the reaction is conducted at a temperature of from about 140° C. to 300° C.

5. A process as recited in claim 2 in which the catalyst concentration in the reaction mixture, with respect to the palladium salt, is in the range of 0.2 to 1 percent, based upon the combined weight of the epoxide compound and organic hydroxy compound reactants in the reaction mixture.

6. A process as recited in claim 5 in which the molar ratio of the palladium salt to the copper salt is in the range of 0.5 to 2.0.

7. A process for the preparation of a hydroxy ether which comprises reacting an epoxide compound selected from the group consisting of ethylene oxide and propylene oxide with an alcohol selected from the group consisting of monohydric alcohols and polyhydric alcohols in the liquid phase, in a molecular oxygen

TABLE 1

Condensation of Alcohols with Ethylene and Propylene Oxides

| Example No. | Alcohol (g)* | Alkene Oxide (g) | Catalyst (mmol)** | Time hr. | Temp., °C. | Products (g) |
|---|---|---|---|---|---|---|
| 1 | $HOCH_2CH_2OH$ (30) | 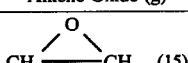 (15) | $PdCl_2$ (1.7) $CuCl_2$ (2.2) | 14 | 150 | $HOCH_2CH_2OH$ (18) $HOCH_2CH_2OCH_2CH_2OCH_2CH_2OH$ (25) |
| 2 | $HOCH_2CH_2OH$ (5) | 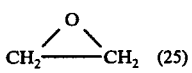 (25) | $PdCl_2$ (1.7) $CuCl_2$ (2.2) | 15 | 150 | $HO(CH_2CH_2O)_n$—H $n = 1$ (2) $n = 3$ (8) $n = 4$ (9) $n = 5$ (7) |
| 3 | $CH_3OH$ (10) | 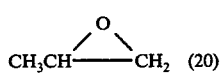 (20) | $K_2PdCl_4$ (0.05) $CuCl_2$ (2.2) | 4.0 | 140 | $CH_3CHCH_2$ (1.7) $\mid\quad\mid$ $OH\ OCH_3$ $CH_3$—OH 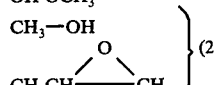 (25) |

*grams
**millimols

The invention being thus described, it will be obvious that the same may be varied in many ways. Such variations are not to be regarded as a departure from the spirit and scope of the invention, and all such modifications are intended to be included within the scope of the following claims.

We claim:

1. A process for the preparation of a hydroxy ether which comprises reacting an epoxide compound having not more than four carbon atoms in the ring with an organic hydroxy compound containing alcoholic or phenolic hydroxy groups in the liquid phase, in a molecular oxygen gaseous atmosphere, and in the presence of a catalytic amount of a catalyst consisting essentially of a palladium salt and a copper salt, at least a portion of the anion of said palladium or copper salt being a chloride ion.

2. A process for the preparation of a hydroxy ether which comprises reacting an epoxide compound selected from the group consisting of 1,2- and 1,3-alkylene oxides with an organic hydroxy compound selected from the group consisting of alcohols and phenols in the gaseous atmosphere, and in the presence of a catalytic amount of a catalyst consisting essentially of cupric chloride ($CuCl_2$) and a palladium salt selected from the group consisting of palladium chloride ($PdCl_2$) and potassium palladium chloride ($K_2PdCl_6$).

8. A process as recited in claim 7 in which the molar range of the epoxide compound to the alcohol is in the range of 0.5 to 10.

9. A process as recited in claim 7 in which the reaction is conducted at a temperature in the range of from about 140° to 300° C.

10. A process as recited in claim 7 in which the catalyst concentration in the reaction mixture, with respect to the palladium salt, is in the range of 0.2 to 1 percent, based upon the combined weight of the epoxide compound and the alcohol reactants in the reaction mixture.

11. A process as recited in claim 10 in which the molar ratio of the palladium salt to the cupric chloride is in the range of 0.5 to 2.0.

12. A process for the preparation of a hydroxy ether having the formula $HO(CH_2CH_2O)_3H$ which comprises reacting ethylene glycol with ethylene oxide in the liquid phase, in a molecular oxygen gaseous atmosphere, and in the presence of a catalytic amount of a catalyst consisting essentially of palladium chloride ($PdCl_2$) and cupric chloride ($CuCl_2$).

13. A process as recited in claim 12 in which the reaction temperature is about 150° C.

14. A process for the preparation of a mixture of hydroxy ethers having the formula $HO(CH_2CH_2O)_nH$, $n$ being equal to 3, 4 and 5, which comprises reacting ethylene glycol with ethylene oxide in the liquid phase, in a molecular oxygen gaseous atmosphere, and in the presence of a catalytic amount of a catalyst consisting essentially of palladium chloride ($PdCl_2$) and cupric chloride.

15. A process as recited in claim 14 in which the reaction temperature is about 150° C.

16. A process for the preparation of a hydroxy ether which comprises reacting methanol with propylene oxide in the liquid phase, in a molecular oxygen gaseous atmosphere, and in the presence of a catalytic amount of a catalyst consisting essentially of $K_2PdCl_4$ and cupric chloride ($CuCl_2$).

17. A process as recited in claim 16 in which the molar ratio of propylene oxide to methanol is about 1.1.

18. A process as recited in claim 17 in which the reaction temperature is about 140° C.

19. A process as recited in claim 1 in which the molar ratio of the palladium salt to the copper salt is in the range of 0.5 to 2.0.

* * * * *